United States Patent
Bodnar et al.

(10) Patent No.: US 11,753,576 B2
(45) Date of Patent: *Sep. 12, 2023

(54) METHOD FOR INHIBITING GAS HYDRATE BLOCKAGE IN OIL AND GAS PIPELINES

(71) Applicant: Clariant International, Ltd., Muttenz (CH)

(72) Inventors: Scot Bodnar, Houston, TX (US); Dan Smith, Spring, TX (US); Felix Hoevelmann, Mühldorf (DE); Corinna Krüger, Kirchheim (DE); Matthias Krull, Harxheim (DE); Jonathan James Wylde, The Woodlands, TX (US); Lisa Greaney Tejada, Spring, TX (US)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/424,161

(22) Filed: May 28, 2019

(65) Prior Publication Data

US 2020/0377783 A1     Dec. 3, 2020

(51) Int. Cl.
*C09K 8/52* (2006.01)
*C07C 233/09* (2006.01)

(52) U.S. Cl.
CPC .............. *C09K 8/52* (2013.01); *C07C 233/09* (2013.01); *C09K 2208/22* (2013.01)

(58) Field of Classification Search
CPC ...... C09K 8/52; C09K 2208/22; C09K 8/524; C07C 233/09; C10L 3/107
See application file for complete search history.

(56) References Cited

U.S. PATENT DOCUMENTS

| | | | |
|---|---|---|---|
| 2004/0214725 A1 | 10/2004 | Moss | |
| 2005/0081432 A1* | 4/2005 | Panchalingam | C10L 3/003 44/419 |
| 2014/0256998 A1 | 9/2014 | Hellsten | |

FOREIGN PATENT DOCUMENTS

| | | |
|---|---|---|
| CN | 101260066 | 9/2008 |
| GB | 2349889 | 11/2000 |
| WO | 2005042675 | 5/2005 |
| WO | 2013048365 | 4/2013 |
| WO | 2015051137 | 4/2015 |
| WO | WO2017/105507 * | 6/2017 |
| WO | 2018115186 | 6/2018 |

OTHER PUBLICATIONS https://en.wikipedia.org/wiki/Coconut_oil downloaed on Mar. 24, 2021.*
"Basically Substituted Aliphatic Nitriles and their Catalytic Reduction to Amines" Frank C. Whitmore, et al., J. Am. Chem. Soc. 1944, 66, 5, pp. 725-731.
International Preliminary Report on Patentability for PCT/EP2020/061457, dated Oct. 7, 2021, 9 pages.
International Preliminary Report on Patentability for PCT/EP2020/061458, dated Oct. 7, 2021, 10 pages.
International Search Report for PCT/EP2020/061457, dated Jul. 20, 2020, 2 pages.
International Search Report for PCT/EP2020/061458, dated Jul. 16, 2020, 2 pages.

* cited by examiner

*Primary Examiner* — Kumar R Bhushan
(74) *Attorney, Agent, or Firm* — Tod A. Waldrop

(57) ABSTRACT

This invention relates to a method for inhibiting the agglomeration of gas hydrates, comprising the injection of an anti-agglomerant comprising a N,N-dialkyl-ammoniumalkyl fatty acid amide represented by the formula (I)

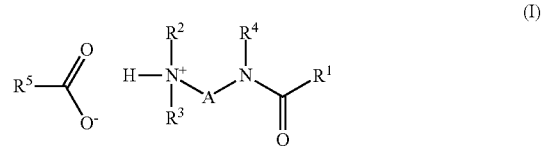

wherein
$R^1$ is an alkyl or alkenyl group having from 7 to 21 carbon atoms,
$R^2$ and $R^3$ are each independently an alkyl group containing 1 to 10 carbon atoms, or together form an optionally substituted ring having 5 to 10 ring atoms, wherein the ring may carry up to 3 substituents,
$R^4$ is hydrogen or an alkyl group having 1 to 6 carbon atoms,
$R^5$ is hydrogen or an optionally substituted hydrocarbyl group having 1 to 17 carbon atoms and
A is an alkylene group having two or three carbon atoms, into a fluid comprising gas, water and oil under conditions prone to the formation of gas hydrates,
wherein the N,N-dialkyl-ammoniumalkyl fatty acid amide represented by the formula (I) is produced by the condensation reaction of a fatty acid with an N,N-dialkylamino alkyl amine and subsequent neutralization with a carboxylic acid.

15 Claims, No Drawings

METHOD FOR INHIBITING GAS HYDRATE BLOCKAGE IN OIL AND GAS PIPELINES

The present invention relates to an improved method for inhibiting the formation of gas hydrate plugs in pipelines, transfer lines and other conduits containing a multiphase mixture comprising water, gas, and condensate, black oil and/or drilling mud. The method comprises the treatment of the multiphase mixture with at least one (N,N-dialkyl-ammoniumalkyl) fatty acid amide produced by condensation of an N,N-dialkylaminoalkylamine with a fatty acid. This method provides reduced dosage rates of the additive. Concurrently the formation of reverse emulsions in downstream separators is diminished leading to improved quality of the water phase to be disposed.

A number of hydrocarbons, especially low molecular weight hydrocarbons with 1 to 6 carbon atoms, are known to form hydrates in conjunction with water present in the system under a variety of conditions—particularly at the combination of lower temperature and higher pressure. In the oil and gas industry such conditions often prevail in equipment that process formation fluids and gases. Usually such hydrates are solids that are essentially insoluble in the fluid itself. Any solids, including hydrates, present in a formation or natural gas fluid are problematic for production, handling and transport of these fluids. The solid hydrates may cause plugging and/or blockage of pipelines, transfer lines and other conduits, of valves and/or safety devices and/or other equipment. This may result in shutdown, lost oil production, pipeline damage, risk of explosion and/or unintended release of hydrocarbons into the environment either on-land or off-shore. Therefore, the formation of gas hydrates poses a safety hazard to field workers and the public. The damage resulting from a blockage can be very costly from an equipment repair standpoint, as well as from the loss of production, and finally the resultant environmental impact. Accordingly, gas hydrates are of substantial interest as well as concern to many industries, particularly the petroleum and natural gas industry.

Gas hydrates are clathrates and are also referred to as inclusion compounds. Clathrates are cage structures formed between a host molecule and a guest molecule. A gas hydrate generally is composed of crystals formed by water host molecules surrounding the hydrocarbon guest molecules. The smaller and lower-boiling hydrocarbon molecules, particularly $C_1$-(methane) to $C_4$ hydrocarbons and their mixtures, are especially problematic because their hydrate or clathrate crystals are easy to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under certain conditions. Thus, when the appropriate conditions are present, hydrates can easily form for example during the transportation of moist respectively wet gas in pipelines.

Modern oil and gas technologies tend to operate under increasingly severe conditions. For example, during the course of drilling operations as well as during oil recovery and production, high pumping speed, high pressure in the pipelines, extended length of pipelines, and low temperature of the oil and gas flowing through the pipelines, for example in subsea operations, are applied. This increases the frequency of formation of gas hydrates.

There are two basic techniques to overcome or control the gas hydrate problems, namely thermodynamic and kinetic. For the thermodynamic approach a number of methods have been reported, including water removal, temperature increase, pressure decrease, addition of "antifreeze" to the fluid and/or a combination of these (known in the industry as Thermodynamic Hydrate Inhibitors and abbreviated THI). The kinetic approach generally attempts to inhibit and/or to retard initial gas hydrate crystal nucleation and/or further crystal growth (known in the industry as a Kinetic Hydrate Inhibitor and abbreviated KHI). Thermodynamic and kinetic hydrate control methods may be used in conjunction.

The amount of chemical needed to prevent blockages varies widely depending upon the type of inhibitor employed. Thermodynamic hydrate inhibitors are substances that can reduce the temperature at which the hydrates form at a given pressure and water content. The most commonly used classes of THIs are alcohols as for example methanol and ethanol, and glycols as for example ethylene glycol, diethylene glycol and glycerin. They are typically used at very high concentrations (regularly dosed as high as 50 wt.-% based on water content, with ethylene glycol often being used in amounts equal to the weight of water present in the system). Therefore, there is a substantial cost associated with the provision, transportation and storage of large quantities of these solvents. The use of kinetic hydrate inhibitors is a more cost-effective alternative as they generally require a dose of less than about 2 wt.-% based on the water content to inhibit the nucleation and/or growth of gas hydrates. Kinetic hydrate inhibitors are often also labeled Low Dosage Hydrate Inhibitors (abbreviated LDHI).

Besides the kinetic hydrate inhibitors (KHIs) there is a closely related second general type of LDHIs, the so-called Anti-Agglomerants (abbreviated AA). While KHIs work by delaying the growth of gas hydrate crystals and may function as "anti-nucleators", AAs allow hydrates to form but prevent them from agglomerating and subsequently from accumulating into larger aggregates capable of causing plugs. Often AAs prevent the once formed smaller gas hydrate crystals to adhere to the pipe wall.

Kinetic efforts to control hydrates have included the use of different chemicals as inhibitors. Typically, KHIs are low molecular weight polymers that adsorb on gas hydrate crystal faces and interfere with the nucleation and growth of gas hydrate crystals. For instance, polymers comprising lactam rings (stemming e.g. from vinyl caprolactam) have been employed to control clathrate hydrates in fluid systems. Similarly, onium compounds with at least four carbon substituents are used to inhibit the plugging of conduits by gas hydrates. Unfortunately, there are several limitations that have been discovered with the use of KHIs such as sub-cooling limits, solubility problems based on temperature and salt content of the water, and chemical incompatibility with the system being treated.

Anti-agglomerants typically are surface active molecules (amphiphiles). Without wishing to be bound to this theory, it has been hypothesized that when small gas hydrate crystals begin to form, AAs attach to them via their polar headgroup. This makes the surface hydrophobic, which mediates the capillary attraction between the crystals and water and fosters dispersion of the crystals in a liquid hydrocarbon phase. This results in a relatively stable and transportable hydrate slurry in a liquid hydrocarbon phase that can flow to the processing facility. AAs are usually added at dose rates of less than 0.5 wt.-% and up to 2.0 wt.-% based on the water phase.

Besides some polymeric substances and especially nitrogen-containing polymers many different monomeric substances have been described to work as anti-agglomerant.

Quaternary amine chemistry has been proven to be especially effective as anti-agglomerant for hydrate control. The best performing AAs are quaternary ammonium surfactants in which the ammonium headgroup has two or three butyl or pentyl groups attached to the quaternary nitrogen.

A variety of approaches to optimize the performance of anti-agglomerants by modifying the structure of hydrophilic and lipophilic groups and their balance have been made.

GB 2349889 discloses a method for inhibiting the formation and agglomeration of gas hydrates in a fluid containing hydrate forming constituents by adding to the hydrate forming fluids an additive comprising one or more amide compounds of molecular weight less than 1.000.

WO 2005/042675 discloses a method and an amide composition used therein for inhibiting, retarding, mitigating, reducing, controlling and/or delaying the formation of gas hydrates or agglomerates of gas hydrates. The disclosure encompasses the amides obtained by reaction of an N,N-dialkyl-aminoalkylamine with an ester or glyceride as for example a vegetable oil or tallow oil and subsequent reaction with a reactant selected from an alkyl halide, hydrogen peroxide and an acid selected from mineral acids and specific carboxylic acids.

WO 2013/048365 discloses an anti-agglomerate hydrate inhibitor composition, comprising a reaction product of an organic amine and an acid selected from the group consisting of non-halide-containing inorganic acids and organic acids, and mixtures thereof, wherein the reaction product is substantially free of halides containing compounds. The halide free AA-LDHI compositions are not as corrosive as the likes of HCl or HX, do not cause halide stress cracking, and are not as toxic.

WO 2017/105507 discloses high temperature hydrate inhibitors and methods of using such compositions to inhibit the formation of gas hydrate agglomerates. The inhibitor comprises an amide obtained by reaction of N,N-dialkyl-aminopropylamine with one or more fatty acids or fatty acid esters and subsequent neutralization with an organic sulfonate, e.g. methane sulfonic acid, respectively quaternization with an organic sulfate, e.g. diethylsulfate. These LDHIs are halogen free and may be exposed to temperatures above 200° F. (93° C.) for an extended period of time without substantially degrading.

WO 2018/115186 discloses a method for inhibiting the formation of gas hydrates in systems comprising mixture of hydrocarbons and water, comprising the addition of an alkyl sulfate or alkyl carbonate or carbonate salt of a quaternary ammonium amide with a relatively short fatty chain.

However, upon application of quaternary ammonium surfactants, separation of the multiphase fluids and the water quality obtained thereby are industrial-wide technical challenges, therefore thwarting its broad field implementation to replace conventional THI methods. Often anti-agglomerants cause reverse emulsion problems in separators topside. This includes both free droplets of oil in water and condensed mesophases at the interface comprising surface active salts of naphthenic acids from the oil phase. Thus, there is the desire for LDHIs which give an improved water quality upon separation of the multiphase mixture comprising oil, gas and water phase under conditions no longer prone to hydrate formation, e.g. prior to further processing of the gas and oil phases. Besides easier disposal of the separated water phase this will concurrently raise the production rate of oil and gas. Another drawback of current anti-agglomerants is their high viscosity. Anti-agglomerants are usually injected at the wellhead or even into the formation. Especially in deepwater applications this often requires transportation in tight umbilicals over long distances at low temperatures of about 4° C. or below which necessitates high dilution of the additive and/or high pumping power. Accordingly, there is a demand for anti-agglomerants with a reduced viscosity which allow for lower pumping power and/or higher concentration of the anti-agglomerant. Furthermore, it is desirable if new gas hydrate inhibitors were discovered which yield improved performance over known gas hydrate inhibitors. Accordingly, there is a constant strive for more efficient LDHIs which require lower dosage rates while maintaining effective hydrate inhibition. Similarly, there is an ambition for new synthetic routes for gas hydrate inhibitors having improved economics.

Accordingly, there is an ongoing need for compositions and methods that effectively prevent agglomeration of gas hydrates especially in oil and gas transportation and handling processes. Particularly there is a need for anti-agglomerants which need lower dosage rates to ensure effective hydrate inhibition. Similarly, there is a need for anti-agglomerants which allow for improved handling especially in deepwater applications, i.e. which have a reduced viscosity. Furthermore, a means to mitigate the environmental impact of the use of a gas hydrate inhibitor by improvement of the water quality obtained upon separation of the multiphase mixture into its components is sought.

Surprisingly it was found that salts of N,N-dialkyl-ammoniumalkyl fatty acid amides as described in WO 2005/042675 prevent gas hydrate agglomeration more effectively when produced from N,N-dialkylaminoalkylamine and a fatty acid. Furthermore, upon separation of the multiphase mixture into its components there is only little or even no formation of reverse emulsion of oil in the water phase and the interface shows only little or even no emulsion. Surprisingly, solutions of the anti-agglomerants produced according to the invention have a reduced viscosity especially at low temperatures.

Accordingly, in a first aspect of the invention there is provided a method for inhibiting the agglomeration of gas hydrates, comprising the addition of an anti-agglomerant comprising a N,N-dialkyl-ammoniumalkyl fatty acid amide represented by the formula (I)

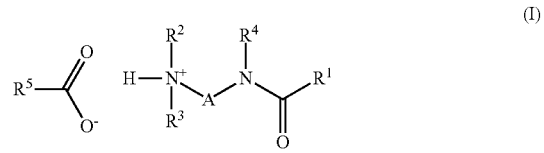

wherein
$R^1$ is an alkyl or alkenyl group having from 7 to 21 carbon atoms,
$R^2$ and $R^3$ are each independently an alkyl group containing 1 to 10 carbon atoms, or together form an optionally substituted ring having 5 to 10 ring atoms, wherein the ring may carry up to 3 substituents,
$R^4$ is hydrogen or an alkyl group having 1 to 6 carbon atoms,
$R^5$ is hydrogen or an optionally substituted hydrocarbyl group having 1 to 22 carbon atoms and
A is an alkylene group having two or three carbon atoms, to a mixture comprising gas, water and oil under conditions prone to the formation of gas hydrates,
wherein the N,N-dialkyl-ammoniumalkyl fatty acid amide represented by the formula (I) is produced by the condensation reaction of a fatty acid with an N,N-dialkylamino alkyl amine and subsequent neutralization with a carboxylic acid.

In a second aspect of the invention there is provided the use of an anti-agglomerant comprising a N,N-dialkyl-ammoniumalkyl fatty acid amide represented by the formula (I)

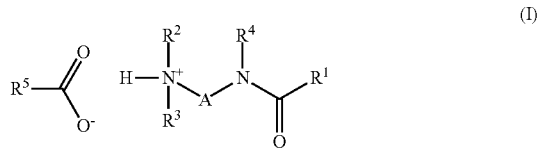

wherein
- $R^1$ is an alkyl or alkenyl group having from 7 to 21 carbon atoms,
- $R^2$ and $R^3$ are each independently an alkyl group containing 1 to 10 carbon atoms, or together form an optionally substituted ring having 5 to 10 ring atoms, wherein the ring may carry up to 3 substituents,
- $R^4$ is hydrogen or an alkyl group having 1 to 6 carbon atoms,
- $R^5$ is hydrogen or an optionally substituted hydrocarbyl group having 1 to 22 carbon atoms and
- A is an alkylene group having two or three carbon atoms, for inhibiting the agglomeration of gas hydrates in a mixture comprising gas, water and oil under conditions prone to the formation of gas hydrates, wherein the N,N-dialkyl-ammoniumalkyl fatty acid amide represented by the formula (I) is produced by the condensation reaction of a fatty acid with an N,N-dialkylamino alkyl amine and subsequent neutralization with a carboxylic acid.

In a third aspect of the invention there is provided a fluid containing gas, water, and oil and a gas hydrate anti-agglomerant comprising a N,N-dialkyl-ammoniumalkyl fatty acid amide represented by the formula (I)

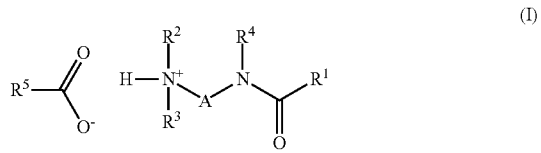

wherein
- $R^1$ is an alkyl or alkenyl group having from 7 to 21 carbon atoms,
- $R^2$ and $R^3$ are each independently an alkyl group containing 1 to 10 carbon atoms, or together form an optionally substituted ring having 5 to 10 ring atoms, wherein the ring may carry up to 3 substituents,
- $R^4$ is hydrogen or an alkyl group having 1 to 6 carbon atoms,
- $R^5$ is hydrogen or an optionally substituted hydrocarbyl group having 1 to 22 carbon atoms and
- A is an alkylene group having two or three carbon atoms, wherein the N,N-dialkyl-ammoniumalkyl fatty acid amide represented by the formula (I) is produced by the condensation reaction of a fatty acid with an N,N-dialkylamino alkyl amine and subsequent neutralization with a carboxylic acid.

In the context of this invention the terms hydrate, hydrocarbon hydrate, gas hydrate and clathrate all refer to solid hydrates of low molecular weight hydrocarbons and water and are used synonymously. The terms anti-agglomerant and gas hydrate anti-agglomerant are used synonymously and refer to substances which inhibit the agglomeration of gas hydrates. The term "inhibiting the agglomeration of gas hydrates" encompasses inhibiting, retarding, reducing, controlling, and/or delaying the formation of hydrates and/or the agglomeration of hydrate crystals.

The N,N-dialkyl-ammoniumalkyl fatty acid amides (I) used in the different aspects of the invention are obtained by the condensation of a fatty acid with a N,N-dialkylaminoalkylamine and subsequent reaction of the intermediate amido amine with a carboxylic acid.

Fatty Acid

Preferred fatty acids as starting material for the production of N,N-dialkyl-ammoniumalkyl fatty acid amides (I) have the formula (III)

wherein $R^1$ is an alkyl or alkenyl group having from 7 to 21 carbon atoms. In a preferred embodiment $R^1$ is an alkyl or alkenyl group having from 9 to 17 carbon atoms and especially preferred having from 11 to 13 carbon atoms, as for example from 9 to 21, or from 9 to 13, or from 7 to 17, or from 7 to 13, or from 11 to 21, or from 11 to 17 carbon atoms. Preferred alkyl groups $R^1$ may be linear or branched. More preferably they are linear. Preferred alkenyl groups $R^1$ may have one or more C=C double bonds as for example one or two C=C double bonds.

Examples for preferred fatty acids (III) are octanoic acid, 2-ethylhexanoic acid, nonanoic acid, iso-nonanoic acid, decanoic acid, neodecanoic acid, undecanoic acid, neoundecanoic acid, dodecanoic acid, dodecenoic acid, neododecanoic acid, tridecanoic acid, iso-tridecanoic acid, tetradecanoic acid, tetradecenoic acid, pentadecanoic acid, hexadecanoic acid, octadecanoic acid, oleic acid and their mixtures. Especially preferred fatty acids are dodecanoic acid, tetradecanoic acid and their mixtures.

In a preferred embodiment a mixture of fatty acids is used. Mixtures of fatty acids may contain for example acids with different chain lengths, with different degrees of unsaturation and/or with different degrees of branching. In preferred fatty acid mixtures at least 60 mol-%, more preferably at least 75 mol-%, most preferred at least 85 mol-% and especially preferred at least 90 mol-% of the alkyl and/or alkenyl residues $R^1$ as for example 60 to 99 mol-%, or 60 to 95 mol-%, or 75 to 99 mol-%, or 75 to 95 mol-%, or 85 to 99 mol-%, or 85 to 90 mol-%, or 90 to 99 mol-%, or 90 to 95 mol-% of the fatty acids of formula (III) have 12 to 14 carbon atoms. In a further preferred embodiment the molar ratio of fatty acids having 12 carbon atoms and fatty acids having 14 carbon atoms is between 20:1 and 1:20, more preferably between 10:1 and 1:10 and especially preferred between 8:1 and 1:1. In a preferred embodiment the fatty acids having 12 to 14 carbon atoms are linear or at least essentially linear, i.e. preferably at least 60 mol-% and more preferably at least 80 mol-% and especially at least 90 mol-% of the fatty acids are linear.

The fatty acids (III) may be of natural or synthetic origin. Especially preferred are mixtures of fatty acids derived from renewable materials as for example palm fatty acid, coco fatty acid, soya fatty acid, sun flower fatty acid, rapeseed fatty acid and tallow fatty acid. A further especially preferred source of fatty acids are fatty acid distillates (FADs) which are also known as acid oils. These are side-streams from processing of natural oils. FADs result from refining of natural oils into food grade oil when their content of degraded components, especially fatty acids, needs to be removed to improve taste, odor, and color of the oil to meet e.g. the food and cosmetics industries' quality standards. The FADs obtained by distillation mainly contain a mixture of free fatty acids but they may contain some acylglycerols. The fatty acid mixtures derived from natural sources may be used as such or upon hydrogenation respectively partial hydrogenation.

Preferred fatty acids and fatty acid mixtures (III), including FADs, have acid numbers determined according to DIN/EN/ISO 2114 of at least 50 mg KOH/g, more preferably between 100 and 390 mg KOH/g and especially preferred between 120 and 320 mg KOH/g as for example between 50 and 390 mg KOH/g, or between 50 and 320 mg KOH/g, or between 100 and 320 mg KOH/g, or between 120 and 390 mg KOH/g. The acid numbers may be determined according to DIN/EN/ISO 2114.

N,N-Dialkylaminoalkylamine

Preferred N,N-dialkylaminoalkylamines as starting material for the production of N,N-dialkyl-ammoniumalkyl fatty acid amides (I) have the general formula (IV)

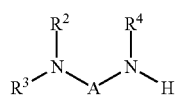

wherein
$R^2$ and $R^3$ are each independently an alkyl group containing 1 to 10 carbon atoms, or together form an optionally substituted ring having 5 to 10 ring atoms, wherein the ring may carry up to 3 substituents,
$R^4$ is hydrogen or an alkyl group having 1 to 6 carbon atoms and
A is an alkylene group having two or three carbon atoms.

In a preferred embodiment $R^2$ and $R^3$ are each independently from another an alkyl group having 2 to 6 carbon atoms, more preferably having 3 to 5 carbon atoms and especially preferred having 3 or 4 carbon atoms, as for example having 1 to 6 carbon atoms, or 1 to 5 carbon atoms, or 1 to 4 carbon atoms, or 2 to 10 carbon atoms, or 2 to 5 carbon atoms, or 2 to 4 carbon atoms, or 3 to 10 carbon atoms, or 3 to 6 carbon atoms. Examples for preferred alkyl groups $R^2$ and $R^3$ are methyl, ethyl, propyl, iso-propyl, n-butyl, iso-butyl, tert.-butyl, and the various isomers of pentyl, hexyl, heptyl, octyl, nonyl and decyl. Especially preferred are linear alkyl groups. $R^2$ and $R^3$ may be different or they may be the same. In a preferred embodiment $R^2$ and $R^3$ both have 3 to 5 carbon atoms. In a further preferred embodiment $R^2$ and $R^3$ both are linear alkyl groups. In a most preferred embodiment $R^2$ and $R^3$ both are linear $C_3$-, $C_4$-, or $C_5$-alkyl groups.

In a further preferred embodiment $R^2$ and $R^3$ together form a ring having 5 to 8 and especially preferred having 5 or 6 ring atoms, including the nitrogen atom carrying the residues $R^2$ and $R^3$. Preferably the further ring atoms are carbon atoms. In a further preferred embodiment the ring comprises, besides carbon atoms, one or two ring atoms selected from N, O and S. Examples for preferred cyclic structures are 1-piperidyl, pyrrolidin-1-yl, piperazin-1-yl and morpholinyl residues. The ring formed by $R^2$ and $R^3$ may be substituted with one, two or three substituents. In a preferred embodiment the ring carries one substituent. Preferred substituents are alkyl residues having 1 to 4 carbon atoms as for example methyl, ethyl, n-propyl, isopropyl, n-butyl, isobutyl and tert.-butyl groups. The substituent may be bound to a carbon atom. Preferably it is bound to a nitrogen atom, if present.

A is an alkylene group having two or three carbon atoms. Preferably A is an ethylene or a propylene group. When A has 3 carbon atoms it may be straight-chain or branched. In a more preferred embodiment A is an ethylene group having the formula $-CH_2-CH_2-$ and in an especially preferred embodiment A is a propylene group having the formula $-CH_2-CH_2-CH_2-$.

Preferably $R^4$ is hydrogen or an alkyl group having 1 to 4 carbon atoms as for example a methyl, ethyl, propyl, isopropyl, butyl, isobutyl or tert.-butyl group.

Especially preferred $R^4$ is hydrogen.

Examples for preferred N,N-dialkylaminoalkyleneamines according to formula (IV) are N,N-dimethylaminoethylamine, N,N-dimethylaminopropylamine, N,N-diethylaminoethylamine, N,N-diethylaminopropylamine, N,N-dipropylaminoethylamine, N,N-dipropylaminopropylamine, N,N-dibutylaminoethylamine, N,N-dibutylaminopropylamine and N,N-dimethylamino-2-hydroxypropylamine, N-(3-aminopropyl)pyrrolidine, N-(3-aminopropyl)piperidine, 1-(3-aminopropyl)-piperazine and 1-(3-aminopropyl)-4-methylpiperazine. The preparation of N,N-dialkylaminoalkylenamines is described for example in Journal of the American Chemical Society 1944, 66(5), 725-731.

In a first reaction step the fatty acid (III) and N,N-dialkylaminoalkylamine (IV) are reacted to give the corresponding N,N-dialkylaminoalkylamino fatty acid amide (II).

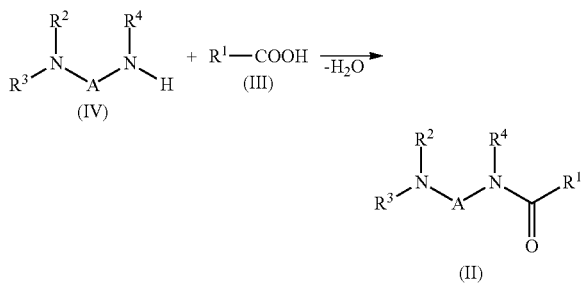

wherein $R^1$, $R^2$, $R^3$, $R^4$ and A have the meanings given above.

In a subsequent reaction step the intermediate N,N-dialkylaminoalkyl fatty acid amide (II) is reacted with a carboxylic acid (V) to give the N,N-dialkyl-ammoniumalkyl fatty acid amide (I).

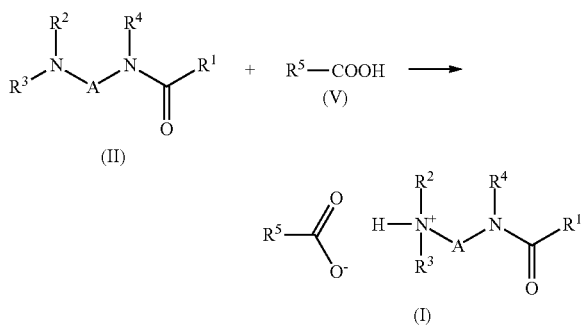

wherein $R^1$, $R^2$, $R^3$, $R^4$, $R^5$ and A have the meanings given above.

Carboxylic Acid

Preferred carboxylic acids for the reaction with the intermediate amido amine (II) have the formula (V)

$$R^5\text{—COOH} \qquad (V)$$

wherein $R^5$ is hydrogen or an optionally substituted hydrocarbyl residue having between 1 and 17 carbon atoms, preferably between 2 and 11 carbon atoms and especially preferred between 2 and 5 carbon atoms as for example between 1 and 11 carbon atoms, or between 1 and 5 carbon atoms, or between 2 and 17 carbon atoms.

In preferred carboxylic acids according to formula (V) the optionally substituted hydrocarbyl residue $R^5$ is an alkyl or alkenyl residue with alkenyl residues having at least two carbon atoms. Preferred alkyl and alkenyl residues may be linear or, having three or more carbon atoms, may be branched. Preferred alkenyl residues $R^5$ have one or more as for example one, two or three double bonds. Preferred substituents are hydroxy groups, carboxylic acid groups and amino groups. Preferred carboxylic acids (V) include natural and synthetic fatty acids. Carboxylic acids based on renewable raw materials are especially preferred. Such fatty acids are obtainable for example by saponification of naturally occurring oils and fats and optionally further derivatization.

Examples for preferred carboxylic acids $R^5$—COOH (V) are formic acid, acetic acid, propionic acid, butyric acid, pivalic acid, hexanoic acid, octanoic acid, 2-ethyl hexanoic acid, decanoic acid neodecanoic acid, undecanoic acid, neoundecanoic acid, dodecanoic acid, neododecanoic acid, tridecanoic acid, iso-tridecanoic acid, tetradecanoic acid, hexadecanoic acid, octadecanoic acid, acrylic acid, methacrylic acid and their mixtures. Mixtures of carboxylic acids may contain acids with different chain lengths, with different degrees of unsaturation and/or different degrees of branching. Especially preferred are mixtures of carboxylic acids based on natural fats and oils as for example coco fatty acid, rape seed fatty acid, soya fatty acid, palm fatty acid, palm kernel fatty acid, tallow fatty acid, and tall oil fatty acid. These carboxylic acid mixtures may be used as such or upon hydrogenation respectively partial hydrogenation. In a preferred embodiment $R^5$ is a saturated $C_1$- to $C_{17}$ alkyl residue and especially preferred a saturated $C_1$- to $C_5$ alkyl residue. In a further especially preferred embodiment $R^5$ is an unsaturated $C_2$- to $C_5$ alkenyl residue. Examples for especially preferred carboxylic acids are acrylic acid, methacrylic acid, acetic acid, propionic acid, dodecanoic acid and coconut fatty acid. The fatty acid used in the first reaction step and the carboxylic acids use in the second reaction step may be the same or different.

In a preferred embodiment most of the starting fatty acid and/or the carboxylic acid are selected from renewable materials. In an especially preferred embodiment all or at least essentially all of the starting fatty acid and/or the carboxylic acid are selected from renewable materials. Accordingly, the hydrate inhibitors according to the invention are considered to be renewable.

Synthesis

For production of the intermediate N,N-dialkylaminoalkyl fatty acid amide (II) the fatty acid (III) maybe reacted with the N,N-dialkylaminoalkylamine (IV) at a temperature of between 100 and 240° C., preferably at a temperature of between 120 and 200° C., as for example between 100 and 200° C. or between 120 and 240° C. The amidation reaction is suitably effected by heating the mixture for a period of from 2 to 20 hours. The pressure is preferably between 0.001 and 1.2 bar and more preferred between 0.01 and 1.0 bar. Often a reduced pressure of from 5 to 200 mbar has proven to be advantageous. Preferably the water formed during the amidation reaction is removed via distillation. In a further preferred embodiment, the water maybe removed by azeotropic distillation in the presence of a solvent forming an azeotrope with water as for example an aromatic hydrocarbon like toluene, xylene or higher boiling aromatics. The degree of reaction can be followed by determination of the acid number, hydrolysis number and/or by the determination of the base and/or amide nitrogen. In a preferred embodiment the condensation to the corresponding N,N-dialkylaminoalkyl fatty acid amide (II) is conducted until no further water of reaction is formed. This indicates a complete or an essentially complete conversion.

In the amidation reaction step preference is given to using essentially equimolar quantities of fatty acid (III) and N,N-dialkylaminoalkylamine (IV). Essentially equimolar proportions include molar ratios between fatty acid (III) and N,N-dialkylaminoalkylamine (IV) of between 3:1 and 1:3, more preferably between 1.5:1 and 1:1.5 and especially preferred between 1.1:1 and 1:1.1, as for example between 3:1 and 1:1.5, or between 3:1 and 1:1.1, or between 1.5:1 and 1:3, or between 1.5:1 and 1:1.1, or between 1.1:1 and 1:3 or between 1.1:1 and 1:1.5. The amidation reaction may include intermediate esterification with a lower alcohol, preferably with a lower monohydric alcohol, followed by aminolysis of the ester thus formed. This may proceed in-situ in a one-pot reaction and may require pressurization of the reaction vessel. Suitable alcohols are, for example, methanol, ethanol, propanol, isopropanol, n-butanol, iso-butanol, tert.-butanol or 2-ethylhexanol. Preference is given to 2-ethylhexanol.

The amidation reaction can be accelerated by addition of suitable acidic catalysts having a pKa of less than or equal to 5, with Bronstedt and Lewis acids being preferred. Examples for suited catalysts are mineral acids as well as organic acids, including but not limited to hydrochloric acid, sulfuric acid, methanesulfonic acid, p-toluenesulfonic acid, dodecyl benzene sulfonic acid, hypophosphorous acid, phosphorous acid, citric acid, $BF_3$ and alkylstannic acids. Typically 0.001 to 0.5 wt.-% and preferably 0.005 to 0.15 wt.-% of the catalyst in respect to the combined masses of the N,N-dialkylaminoalkylamine (IV) and the fatty acid (III) are used. In a first preferred embodiment the catalyst remains in the reaction product. Accordingly, the N,N-dialkylaminoalkyl fatty acid amide (II) may contain up to 1.5 mol-% and especially preferred less than 0.5 mol-% of the catalyst in respect to the N,N-dialkylaminoalkyl fatty acid amide (II). In a second preferred embodiment the catalyst is removed from the amide reaction product after the reaction, e.g. by extraction. In a third preferred embodiment the reaction is made in absence of a catalyst. Accordingly, in the second and third preferred embodiments the N,N-dialkylaminoalkyl fatty acid amide (II) does not contain any catalyst and especially no organic sulfonate.

For production of the N,N-dialkylammoniumalkyl fatty acid amide (I) the intermediate N,N-dialkylaminoalkyl fatty acid amide (II) is reacted with the carboxylic acid (V). Preferably, salt formation is accomplished by mixing the N,N-dialkylaminoalkyl fatty acid amide (II) with an appropriate amount of the carboxylic acid (V) to give the corresponding N,N-dialkylammoniumalkyl fatty acid amide salt (I). Preferably the formation of the salt is made at temperatures between ambient and 100° C. and more preferably at temperatures between 30 and 60° C. Preferably the carboxylic acid (V) is added to the N,N-dialkylaminoalkyl fatty acid amide (II) in a manner that the temperature does not exceed 100° C. and more preferably not 70° C. Preferably the carboxylic acid (V) and the N,N-dialkylaminoalkyl fatty acid amide (II) are reacted in a molar ratio of between 1:10 and 5:1, more preferably between 1:5 and 3:1 and especially preferred between 1:2 and 1:1, as for example between 1:10 and 3:1, or between 1:10 and 1:1, or between 1:5 and 5:1, or between 1:5 and 1:1, or between 1:2 and 5:1, or between 1:2 and 3:1. In a specific embodiment carboxylic acid (V) and N,N-dialkylaminoalkyl fatty acid amide (II) are reacted in equimolar or at least essentially equimolar quantities as for example between 1:1.5 and 1.5:1 or between 1:1.2 and 1.2:1. The given molar ratios refer to the number of carboxylic acid groups of the carboxylic acid (V) and to the amino groups of the N,N-dialkylaminoalkyl fatty acid amide (II).

The reaction sequence can be executed solvent free. However, in many cases it has proven to be advantageous to conduct the reaction or at least one or more of the reaction steps in the presence of a solvent. Especially for the reaction of the fatty acid (III) with the N,N-dialkylaminoalkylamine (IV) the presence of a solvent is preferred when a high conversion and/or a low acid number of the resulting reaction product is targeted. Preferred solvents for the reaction are organic compounds which allow for azeotropic removal of the water of reaction. In particular, aromatic solvents or solvent mixtures, or alcohols, can be used. Particular preference is given to solvents having a boiling point of at least 100° C. and preferably 110 to 200° C. under standard conditions. Examples of suitable solvents are decane, toluene, xylene, diethylbenzene, naphthalene, tetralin, decalin, and commercial solvent mixtures such as Shellsol®, Exxsol®, Isopar®, Solvesso® types, Solvent Naphtha and/or kerosene. In a preferred embodiment, the solvent comprises at least 10% by weight, preferably 20 to 100% by weight, for example 30 to 90% by weight, of aromatic constituents. Shellsol® and Exxsol® grades are obtainable form Shell and ExxonMobil, respectively. The reaction is then effected at the boiling point of the azeotrope.

The thus produced N,N-dialkylammoniumalkyl fatty acid amide salt (I) may be purified by any methods known to the skilled in the art, e.g, by filtration, extraction, distillation or recrystallization. However, in most cases the direct reaction product has proven to be suited for direct application.

The anti-agglomerants of the present disclosure may be used to inhibit, retard, mitigate, reduce, control, and/or delay the formation of one or more hydrates or agglomerates of hydrates. In a preferred embodiment one or more anti-agglomerants of the present disclosure may be introduced into a fluid comprising water, a gas and a liquid hydrocarbon. Although listed separately from liquid hydrocarbon, the gas may in some embodiments include gaseous hydrocarbon, though the gas need not necessarily include hydrocarbon.

The fluids to be inhibited from gas hydrate agglomeration may have different water cuts (i.e., the ratio of the volume of water in the fluid to the total volume of the fluid). For example, the anti-agglomerants according to the disclosure of the invention have been successfully applied in fluids having a water cut of about 1 to about 65 vol.-%. In preferred embodiments, a fluid may have a water cut of 1% or more, 5% or more, 10% or more, 15% or more, 20% or more, 30% or more, 40% or more, 50% or more, or 60% or more.

The method according to the first aspect of the invention and the use according to the second aspect of the invention are especially advantageous in neutral and especially in acidic fluids, i.e. fluids having a pH of below 8.0, more preferably of below 7.5, still more preferably of below 7.0 and especially preferred of below 6.5.

In a preferred embodiment the fluid to be inhibited from gas hydrate agglomeration is a petroleum fluid being the mixture of varying amounts of water/brine, crude oil/condensate, and natural gas. The petroleum fluid may contain various levels of salinity. The fluid can have a salinity of about 0% to about 25% or about 10% to about 25% weight/weight (w/w) total dissolved solids (TDS).

The petroleum fluids in which the gas hydrate anti-agglomerant is applied according to the first and second aspect of the invention can be contained in many different types of apparatuses, especially those that transport an aqueous medium from one location to another. In a preferred embodiment the petroleum fluid is contained in an oil and gas pipeline. In a further preferred embodiment the petroleum fluid to be treated can be contained in refineries, such as separation vessels, dehydration units, gas lines, and pipelines.

For inhibition of gas hydrate agglomeration according to the first and second aspect of the invention the N,N-dialkylammoniumalkyl fatty acid amide salt (I) is injected into the fluid to be inhibited from gas hydrate agglomeration. Preferably, the hydrate anti-agglomerant is injected into the fluid to be inhibited prior to substantial formation of hydrates. The anti-agglomerant may be introduced into the fluid through a conduit or an injection point. In certain embodiments, one or more anti-agglomerants of the present disclosure may be introduced into a wellbore, a conduit, a vessel, and the like and may contact and/or be introduced into a fluid residing therein. An exemplary injection point for petroleum production operations is downhole near the surface controlled sub-sea safety valve. This ensures that during a shut-in, the gas hydrate anti-agglomerant can disperse throughout the area where hydrates will occur. Treatment can also occur at other areas in the wellhead or flowline manifold or the flowline itself, taking into account the density of the injected fluid. If the injection point is well above the hydrate formation point, then the hydrate anti-agglomerant can be formulated with a solvent having a density high enough that the inhibitor will sink in the flowline to collect at the water/oil interface. Moreover, the treatment can also be used in pipelines or anywhere in the system where the potential for hydrate formation exists.

The method according to the first aspect of the invention and the use of the anti-agglomerant according to the second aspect of the invention are equally applicable for fluids which are flowing as well as for fluids which are substantially stationary. Accordingly, the fluid may be within a vessel, or within a conduit (e.g., a conduit that may transport the fluid), or within a subterranean formation and/or a wellbore penetrating a portion of the subterranean formation. Examples of conduits include, but are not limited to, pipelines, production piping, subsea tubulars, process equipment, and the like as used in industrial settings and/or as used in the production of oil and/or gas from a subterranean formation, and the like. The conduit may in certain embodiments penetrate at least a portion of a subterranean formation, as in the case of an oil and/or gas well. In particular embodiments, the conduit may be a wellbore or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located belowground). A vessel or conduit according to other embodiments may be located in an industrial setting such as a refinery (e.g., separation vessels, dehydration units, pipelines, heat exchangers, and the like), or it may be a transportation pipeline.

The gas hydrate anti-agglomerant according to the invention is preferably used in amounts of between 0.01 and 5.0% by weight (based on the weight of the aqueous phase), more preferably in amounts between 0.05 and 3.0 wt.-% and especially preferred in amounts between 0.1 and 1.0 wt.-%, as for example between 0.01 and 3.0 wt.-%, or between 0.01 and 1.0 wt.-%, or between 0.05 and 5.0 wt.-%, or between 0.05 and 1.0 wt.-%, or between 0.1 and 5.0 wt.-% or between 0.1 and 3.0 wt.-%. It will be appreciated by one of ordinary skill in the art that the amount of the anti-agglomerant according to the present invention effective for inhibiting, retarding, reducing, controlling, delaying the formation and/or the agglomeration of hydrates may depend upon, for example, the volume of water in the fluid and/or further additives in the fluid to be treated.

The anti-agglomerants according to the disclosure may be used solely as well as in a formulation containing a solvent and/or further actives which further inhibit the formation of hydrates.

In a first preferred embodiment of the first and second aspect of the invention mixtures of two or more of the anti-agglomerants according to the disclosure of this invention are used. Such mixtures may include two or more N,N-dialkylammoniumalkyl fatty acid amide salts of formula (I) differing in at least one feature of $R^1$, $R^2$, $R^3$, $R^4$, and/or A, for example in the alkyl or alkenyl group $R^1$ of the fatty acid.

In a second preferred embodiment of the first and second aspect of the invention the N,N-(dialkylammoniumalkyl) carboxylic acid amide salt (I) is used in combination with a N,N-(dialkylaminoalkyl)carboxylic acid amide (II). Such formulation may be obtained by mixing of the individual components. Alternatively, such mixture may be obtained by partial neutralization of the N,N-dialkylaminoalkyl fatty acid amide (II) with the carboxylic acid (V). Preferably the portions of both species (II) and (I) in such mixtures are between 100:1 and 1:100, more preferably between 20:1 and 1:20, more preferably between 10:1 and 1:10 and especially preferred between 5:1 and 1:2 as for example between 100:1 and 1:20, or between 100:1 and 1:10, or between 100:1 and 1:2, or between 20:1 and 1:100, or between 20:1 and 1:10, or between 20:1 and 1:2, or between 10:1 and 1:100, or between 10:1 and 1:20, or between 10:1 and 1:2, or between 5:1 and 1:100, or between 5:1 and 1:20, or between 5:1 and 1:10.

In the first and second preferred embodiment above the mixtures of anti-agglomerants are used with the same preferred overall dosage rates as disclosed above for a single anti-agglomerant according to the disclosure. However, often such mixtures allow for a reduction of the overall dosage rate.

In a third preferred embodiment of the first and second aspect of the invention, the anti-agglomerants according to the disclosure of the invention are used as a formulation in an organic solvent. This facilitates the handling of the inhibitors and furthermore it often supports dispersion of the hydrate crystals. In a preferred embodiment an alcoholic solvent such as a water-soluble monoalcohol, for example methanol, ethanol, propanol, butanol, an oxyethylated monoalcohol such as butyl glycol, isobutyl glycol, butyl diglycol, a polyglycol, or a mixture thereof is particularly preferred. In a further preferred embodiment; a hydrocarbon containing a carbonyl group such as a ketone, for example acetone, methyl ethyl ketone (2-butanone), methyl propyl ketone, methyl isopropyl ketone, methyl butyl ketone, methyl isobutyl ketone (MIBK), diisobutyl ketone (DIBK), cyclopentanone, cyclohexanone, or a mixture thereof is a particularly preferred solvent. In a further preferred embodiment a higher boiling aliphatic, aromatic or alkylaromatic hydrocarbon, or a mixture thereof has proven to be advantageous. Examples of suitable solvents are decane, toluene, xylene, diethylbenzene, naphthalene, tetralin, decalin, and commercial solvent mixtures such as Shellsol®, Exxsol®, Isopar®, Solvesso® types, diesel, Solvent Naphtha and/or kerosene. In a preferred embodiment, the solvent comprises at least 10% by weight, preferably 20 to 100% by weight, for example 30 to 90% by weight, of aromatic constituents. Shellsol® and Exxsol® grades are obtainable form Shell and ExxonMobil, respectively.

In a preferred embodiment the major part of the anti-agglomerant formulation is a solvent, and in some cases the anti-agglomerant formulation includes up to 50% by weight of a solvent. In a preferred embodiment a solvent is present in the anti-agglomerant formulation on a weight basis of from 0.01 to 70%, more preferably from 0.1 to 50%, even more preferably from 0.5 to 30%, and especially preferred from 1.0 to 25%. In some embodiments a solvent can be present at from 1.5 to 20%, or from 2.0 to 15%, or from 2.5 to 10%, or even from 5 to 10%.

For example, the anti-agglomerant formulation may contain 10 to 30 percent by weight of the N,N-dialkylammoniumalkyl fatty acid amide salt (I) and 70 to 90 percent by weight of a solvent such as methanol. As a further example, the anti-agglomerant formulation may contain 10 to 30 percent by weight of the N,N-dialkylammoniumalkyl fatty acid amide salt (I), 10 to 30 percent by weight of a polymeric kinetic inhibitor, 20 to 40 percent by weight of water, and 20 to 40 percent by weight of ethylene glycol.

In a preferred embodiment the composition is essentially free of glycerol. Essentially free of glycerol means that the composition contains less than 1 wt.-%, preferably less than 0.1 wt.-% and especially preferred no glycerol.

In a further preferred embodiment agglomeration of gas hydrates is inhibited by injection of a combination of the anti-agglomerants of the formula (I) and optionally (II) together with one or more polymers known to inhibit the formation and/or agglomeration of hydrates in order to further improve the performance of the method according to the disclosure, as for example to reduce the overall dosage rate. Preferred further hydrate inhibitors are polymers having a carbon backbone and amide bonds in the side chains. These include in particular homo- and copolymers based on vinylpyrrolidone, vinylcaprolactam, isopropylacrylamide, acryloylpyrrolidine, N-acryloylmorpholine, N-acryloylpiperidine and/or N-methyl-N-vinylacetamide, and optionally containing further anionic, cationic and neutral comonomers having a vinylic double bond, such as for example 2-dimethylaminoethyl methacrylate, 1-olefins, N-alkylacrylamides, N-vinylacetamide, acrylamide, sodium 2-acrylamido-2-methyl-1-propanesulfonate (AMPS) or acrylic acid.

When mixtures of anti-agglomerants according to the disclosure are used in combination with further polymeric gas hydrate inhibitors, the concentration ratio between the anti-agglomerants according to the disclosure of the invention and the mixed-in polymers is preferably between 90:10 and 10:90 percent by weight, more preferably between 75:25 and 25:75, and especially between 60:40 and 40:60 as for example between 90:10 and 25:75, or between 90:10 and 40:60, or between 75:25 and 10:90, or between 75:25 and 40:60, or between 60:40 and 10:90, or between 60:40 and 25:75.

Usually such mixtures allow for further reduction of the treat rate of the gas hydrate inhibitor according to the disclosure and preferably they allow for a reduction of the overall dosage rate. When the anti-agglomerants according to the disclosure are used in a mixture with a polymeric gas hydrate inhibitor, the overall concentration of the mixed inhibitors is from 0.01 to 2% by weight or from 0.02 to 1% by weight, in the aqueous phase to be treated.

In a preferred embodiment agglomeration of gas hydrates is inhibited by injection of the anti-agglomerants of the formula (I) and optionally formula (II) together with one or more thermodynamic gas hydrate inhibitors in order to further improve the performance of the method according to the invention, as for example to further reduce the dosage rate of the anti-agglomerant according to formula (I) and optionally formula (II), to reduce the amount of thermodynamic gas hydrate inhibitor, or to reduce both. While the thermodynamic gas hydrate inhibitor shifts the crystalline equilibrium to lower temperatures the anti-agglomerant according to the disclosure will reduce or even inhibit the agglomeration of once formed crystallites. Preferred thermodynamic gas hydrate inhibitors are alcohols as for example methanol, ethanol and/or ethylene glycol. The preferred dosage rate of thermodynamic gas hydrate inhibitors is between 10 and 60 vol.-% and especially between 20 and 50 vol.-% as for example between 10 and 50 vol.-%, or between 20 and 60 vol.-% in respect to the aqueous phase to be treated. The preferred dosage rate of the anti-agglomerant according to formula (I) and optionally formula (II) is as outlined for these anti-agglomerants above. However, the dosage rate of at least one of the thermodynamic gas hydrate inhibitor and/or the anti-agglomerant according to the disclosure is lower than its dosage rate required upon its individual use.

In a further preferred embodiment the fluid to which one or more anti-agglomerants of the present disclosure is introduced may comprise any number of additional additives. Examples of such additional additives include, but are not limited to, salts, surfactants, proppant particulates, diverting agents, fluid loss control additives, nitrogen, carbon dioxide, surface modifying agents, foamers, corrosion inhibitors, scale inhibitors, wax inhibitors, catalysts, clay control agents, biocides, friction reducers, antifoam agents, flocculants, $H_2S$ scavengers, $CO_2$-scavengers, oxygen scavengers, lubricants, viscosifiers, emulsion breakers, weighting agents, relative permeability modifiers, resins, wetting agents, and the like. A person skilled in the art, with the benefit of this disclosure, will recognize the types of additives that may be included in the fluids of the present disclosure for a particular application In a preferred embodiment agglomeration of gas hydrates is inhibited by injection of the anti-agglomerant of formula (I) and optionally formula (II) according to the invention into a wellbore, a subterranean formation, a vessel, and/or a conduit (and/or into a fluid within any of the foregoing) using any method or equipment known in the art. For example, agglomeration of gas hydrates may be inhibited by injection of the anti-agglomerant into a subterranean formation and/or into a wellbore using batch treatments, squeeze treatments, continuous treatments, and/or any combination thereof. In certain embodiments, a batch treatment may be performed in a subterranean formation by stopping production from the well and pumping an anti-agglomerant formulation into the wellbore, which may be performed at one or more points in time during the life of a well. In other embodiments, a squeeze treatment may be performed by dissolving the anti-agglomerant in a suitable solvent at a suitable concentration and squeezing that formulation downhole into the formation, allowing production out of the formation to bring the anti-agglomerant to its desired location. In another preferred embodiment the anti-agglomerant may be injected into a portion of a subterranean formation using an annular space or capillary injection system to continuously introduce the anti-agglomerant into the formation. In all these embodiments the reduced viscosity of concentrated solutions of the N,N-dialkylammoniumalkyl fatty acid amide salt (I) produced by amidation of a fatty acid according to the disclosure of this invention allows for a lower pumping pressure and/or a higher concentration of the N,N-dialkylammoniumalkyl fatty acid amide salt (I) and therefore requires less volume to be pumped.

In a further preferred embodiment, a composition (such as a treatment fluid) comprising the anti-agglomerant according to the present disclosure may be circulated in the wellbore using the same types of pumping systems and equipment at the surface that are used to introduce treatment fluids or additives into a wellbore penetrating at least a portion of the subterranean formation.

Prior to further downstream processing of the valuable hydrocarbon portion of the multiphase fluid the multiphase fluid may be separated into its components. Such separation may occur in a separator for example in a terminal or in a refinery, leaving an aqueous phase for disposal. The multiphase fluid treated with a N,N-dialkylammoniumalkyl fatty acid amide salt (I) produced by amidation of a fatty acid according to the disclosure of the invention produces a clear water phase with only little or even no emulsion at the oil-water interface and with only little or even no oil emulsified in the water phase. This allows for faster separation of the oil and water phases. Furthermore, it enhances the productivity of oil and reduces the efforts for disposal of the aqueous phase.

Hydrocarbons in the context of this invention are organic compounds which are constituents of mineral oil/natural gas, and their conversion products. Hydrocarbons in the context of this invention are also volatile hydrocarbons, for example methane, ethane, propane, butane. For the purposes of this invention, they also include the further gaseous constituents of crude oil/natural gas, for instance hydrogen sulfide and carbon dioxide.

All percent values are given in percent by weight unless otherwise specified.

EXAMPLES

Materials Used:

For synthesis of the N,N-dialkylammoniumalkyl fatty acid amides the fatty acids, N,N-dialkylaminoalkylamines and solvents characterized in table 1 were used. They were of commercial grades.

TABLE 1

Characterization of reactants and solvents used

| | |
|---|---|
| Coco fatty acid | Mixture of fatty acids based on coconut oil; comprising $C_8$—$C_{18}$ fatty acids being partially unsaturated, wherein 47 wt.-% is $C_{12}$ saturated fatty acid; acid number 275 mg KOH/g |
| Hydrogenated coco fatty acid | Mixture of $C_8$—$C_{18}$ saturated fatty acids, comprising 48 wt.-% $C_{12}$ saturated fatty acid, having <2 wt.-% of unsaturated acids; acid number 270 mg KOH/g |

TABLE 1-continued

Characterization of reactants and solvents used

| | |
|---|---|
| $C_{8/10}$ fatty acid | Mixture of fatty acids containing >80% $C_8$ and $C_{10}$ essentially saturated fatty acids; acid number 364 mg KOH/g |
| $C_{12}$ fatty acid | $C_{12}$ fatty acid, saturated (>95% purity); acid number 281 mg KOH/g |
| Oleic acid | $C_{18}$ fatty acid, unsaturated (>95% purity); acid number 198 mg KOH/g |
| Acid oil | partially hydrolysed sunflower oil (mainly oleic and linoleic acid) with an acid number of 151 mg KOH/g and saponification value of 190 mg KOH/g |
| Coconut oil | Triglyceride of $C_8$—$C_{18}$ fatty acids, comprising as main components 45% $C_{12}$ saturated fatty acid and 9% unsaturated fatty acids. Free fatty acids content was <1%. |
| DBAPA | N,N-Dibutylamino propyl amine (≥98%) |
| DMAPA | N,N-Dimethylamino propyl amine (>98%) |
| DEAPA | N,N-Diethylamino propyl amine (>98%) |
| MSA | methane sulfonic acid |
| Solvent Naphtha (SN) | Mixture of aromatic hydrocarbons having carbon numbers predominantly in the range of $C_9$ through $C_{11}$ and boiling in the range of from 177° C. to 216° C. |

Acid numbers were determined according to DIN/EN/ISO 2114. Saponification numbers were determined according to DIN/EN/ISO 3681.

Starting from the raw materials characterized in table 1 the N,N-dialkylammoniumalkyl fatty acid amides were produced according to either of the following general procedures A or B.

Reaction Pathway A (Ambient Pressure):

A 4-necked flask, equipped with a Dean-Stark apparatus, overhead stirrer, thermometer and nitrogen-purging line was charged with the fatty acid and the N,N-dialkylaminoalkylamine. The mixture was heated to 140-180° C. for a period of 6 to 12 hours during which water was removed from the reaction mixture. The conversion was monitored by means of acid value titration; the reaction was stopped when an acid value of <8 mg KOH/g was obtained. The comparative examples (using triglycerides) were stopped when a primary amine number of less than 15 mg KOH/g was obtained.

Reaction Pathway B (Applying Vacuum):

A 4-necked flask, equipped with a Dean-Stark apparatus, overhead stirrer, thermometer and nitrogen-purging line was charged with the fatty acid and the N,N-dialkylaminoalkylamine. The mixture was heated to 140-160° C. for a period of 2 hours at ambient pressure. Afterwards, vacuum was applied (200±10 mbars) to drive the reaction to completion within another 2-4 hours. The reaction progress and the conversion were monitored by means of acid value titration; the reaction was stopped when an acid value <8 mg KOH/g was obtained.

Following the condensation reaction according to either of reaction pathways A or B and cooling of the reaction product to below 80° C. the reaction product was diluted with a solvent (methanol or solvent naphtha). Subsequently the organic acid was added in such a manner that the temperature of the reaction mixture did not exceed 50° C. to form the final N,N-(dialkylammoniumalkyl)carboxylic acid amide salt. Details of the various syntheses are given in table 2.

TABLE 2

Reactants and reaction pathways for the preparation of N,N-dialkylaminoalkyl fatty acid amides (II) and N,N-(dialkylammoniumalkyl)carboxylic acid amide salts (I)

| | N,N-dialkylaminoalkyl fatty acid amide (II) | | | | Ammonium salt (I) | | Solution | |
|---|---|---|---|---|---|---|---|---|
| Ammonium salt | fatty acid source (III) | N,N-dialkylamino-alkylamine (IV) | molar ratio (III):(IV) | reaction pathway | carboxylic acid (V) | molar ratio (II):(V) | solvent | active concent |
| AS 1 | coco fatty acid | DBAPA | 1:1 | A | acrylic acid | 1:1 | methanol | 85% |
| AS 2 | coco fatty acid | DBAPA | 1:1 | A | acrylic acid | 1:1 | SN | 85% |
| AS 3 | coco fatty acid | DBAPA | 1:1 | B | acrylic acid | 1:1 | methanol | 60% |
| AS 4 | coco fatty acid | DBAPA | 1:1 | B | acetic acid | 1:1 | ethylene glycol | 60% |
| AS 5 | coco fatty acid | DMAPA | 1:1 | A | acrylic acid | 1:1 | methanol | 60% |
| AS 6 | coco fatty acid | DEAPA | 1:1 | A | acrylic acid | 1:1 | methanol | 60% |
| AS 7 | hydrogenated coco fatty acid | DBAPA | 1:1 | B | acrylic acid | 1:1 | methanol | 60% |
| AS 8 | $C_{8/10}$ acid | DBAPA | 1:1 | A | acrylic acid | 1:1 | methanol | 60% |
| AS 9 | oleic acid | DBAPA | 1:1.5 | A | methacrylic acid | 1:1 | SN | 50% |
| AS 10 | $C_{12}$ acid | DBAPA | 1:1 | A | lauric acid | 1:0.8 | methanol | 60% |
| AS 11 | oleic acid | DBAPA | 1:1 | A | propionic acid | 1:1 | SN | 60% |
| AS 12 | acid oil | DBAPA | 1:1 | A | acrylic acid | 1.5:1 | methanol | 85% |
| AS 13 (comp.) | coconut oil | DBAPA | 1:1 | A | acrylic acid | 1:1 | methanol | 85% |
| AS 14 (comp.) | coconut oil | DBAPA | 1:1 | A | acrylic acid | 1:1 | SN | 85% |
| AS 15 (comp.) | Coconut oil | DBAPA | 1:1 | A | acetic acid | 1:1 | methanol | 60% |
| AS 16 (comp.) | $C_{12}$ acid | DBAPA | 1:1 | A | MSA | 1:1 | SN | 60% |

The dynamic viscosities of the samples according to table 1 were determined by using a rheometer from Anton-Paar at the given temperature at a shear rate of $106 \cdot s^{-1}$. The results are given in table 3.

TABLE 3

Viscosities of the N,N-(dialkylammoniumalkyl)carboxylic acid amide salts measured in different solvents

| Example | N,N-(dialkyl-ammoniumalkyl) carboxylic acid amide salt | solvent | active content | Viscosity @10° C. | Viscosity @20° C. |
|---|---|---|---|---|---|
| 1 | AS 3 | methanol | 60% | 1 | <1 |
| 2 | AS 4 | methanol | 60% | 1 | <1 |
| 3 | AS 5 | methanol | 60% | 2 | <1 |
| 4 | AS 6 | methanol | 60% | 2 | <1 |
| 5 | AS 7 | methanol | 60% | 5 | 2 |
| 6 | AS 8 | methanol | 60% | <1 | <1 |
| 7 | AS 9 | methanol | 60% | 8 | 3 |
| 8 | AS 10 | methanol | 60% | 12 | 4 |
| 9 | AS 11 | SN | 60% | 103 | 53 |
| 10 (comp.) | AS 16 (comp.) | SN | 60% | 123 | 72 |
| 11 (comp.) | AS 15 (comp.) | methanol | 60% | 22 | 5 |
| 12 | AS 12 | methanol | 85% | 205 | 125 |
| 13 | AS 1 | methanol | 85% | 162 | 105 |
| 14 (comp.) | AS 13 (comp.) | methanol | 85% | 295 | 144 |
| 15 | AS 2 | SN | 85% | 450 | 202 |
| 16 (comp.) | AS 14 (comp.) | SN | 85% | 835 | 365 |

For evaluation of the performance of the presently disclosed N,N-dialkylammoniumalkyl fatty acid amide salts (I) as low dose gas hydrate inhibitors, a rocking cell test was used. The rocking cell test is a commonly used test in the art for assessing the performance of anti-agglomerant chemistry. Briefly, additives are evaluated based on their ability to effectively minimize the size of hydrate particle agglomerates and then to disperse those particles into the hydrocarbon phase. The results were classified as "pass" or "fail" based on whether hydrate blockages were detected. Performance is evaluated by determining the minimum effective dose (MED) required to register as a "pass" in the rocking cell test. The effective dosages (MEDs) were screened for 5.0 wt.-% NaCl brine at 50 vol.-% water cut and 138 bar at 4° C.

The rocking cell apparatus ("rack") is comprised of a plurality of sapphire tubes, each placed within a stainless-steel support cage. Each assembled sapphire tube and steel cage (hereby referred to as a rocking cell) is typically loaded with a fluid containing a hydrocarbon phase and a brine phase, along with a stainless-steel ball for mixing. The rocking cell can withstand pressures of up to 200 bar (2900 psi). The rocking cell, once loaded with the fluids, is then mounted on the rack with gas injection and pressure monitoring. During testing, as the gases cooled, and hydrates formed, the consumed gas was substituted via a high-pressure syringe pump to maintain the system at constant pressure.

The rack was loaded with 10 rocking cells in a 2×5 configuration (two cells wide and 5 cells tall). The center position on the rack (between two cells) was fixed and allowed to rotate while the outer positions on the rack were moved vertically up and down. This vertical motion allowed the rocking cells to rotate into a positive or negative angle position. The steel ball placed inside the sapphire tube moved from one end of the cell to the other during a rocking motion. The rack rocked up and down at a rate of about 5 complete cycles (up and down) every minute. The rack was further contained within a temperature-controlled bath attached to a chiller with temperature control from −10° C. to 60° C.

The rocking cells were filled with three components: hydrocarbon, aqueous phase, and gas. First, each rocking sapphire tube was filled with 5 ml of dodecane and a 5 ml of 5% NaCl brine (water cut 50 vol.-%) for a total liquid loading of 50% total tube volume (20 mL total). The anti-agglomerants according to table 2 were added at dose rates in volume percent by volume of water. Green Canyon gas was used for this testing with its composition given in Table 4.

TABLE 4

Green Canyon gas composition

| Component Name | Chemical Symbol | Amount (mol) |
|---|---|---|
| Nitrogen | $N_2$ | 0.14 |
| Carbon Dioxide | $CO_2$ | 0 |
| Methane | $C_1$ | 87.56 |
| Ethane | $C_2$ | 7.6 |
| Propane | $C_3$ | 3 |
| i-Butane | $i-C_4$ | 0.5 |
| n-Butane | $n-C_4$ | 0.8 |
| i-Pentane | $i-C_5$ | 0.2 |
| n-Pentane | $n-C_5$ | 0.2 |

Rocking Cell Test Procedure:
A. Pretest Steps: Once the rack has been loaded with the rocking cells containing hydrocarbon fluid, brine and the anti-agglomerant, the rocking cells are evacuated with a vacuum pump for 15-20 minutes. While evacuating, the bath temperature is increased to the starting test temperature of 49° C. Once the bath has reached 49° C., the cells and the syringe pump are pressurized with Green Canyon gas to 138 bar and the syringe pump is switched on to maintain pressure during initial saturation.
B. Saturation Step: The apparatus is set to rock at 5 rocks per minute for 2 hours to ensure the hydrocarbon fluids and brine loaded in the cell have been saturated with gas. This testing is performed at constant pressure and the syringe pump remains switched on and set at 138 bar for the remainder of the test.
C: Cooling Step: While maintaining a rocking rate of 5 rocks per minute, the system is cooled from 49° C. to 4° C. over 6 hours.
D. Steady State Mixing Step before Shut-in: At the constant temperature of 4° C., the apparatus is kept rocking at 5 rocks per minute for 12 hours to ensure complete hydrate formation.
E. Shut-in Step: The apparatus is set to stop rocking and to set the cell position to horizontal and kept at a constant temperature of 4° C. for 12 hours.
F. Steady State Mixing Step after Shut-in: At the conclusion of the shut-in period, the apparatus is restarted at the rate of 5 rocks per minute at the constant temperature of 4° C. for 4 hours.
G. Test Completion: At the conclusion of the experiment, the apparatus is set to stop rocking and the cells are set at a negative inclination to keep fluids away from the gas injection port. The chiller bath is set to 49° C. to melt any formed hydrates and allow for depressurization and cleaning.

To determine the relative performance of each inhibitor or dose rate of inhibitor, visual observations were made during the steady state mixing step after shut-in (period F) and correlated with an interpretation of the time required for the ball within the cell to travel between two magnetic sensors. Each experiment was conducted in duplicate to confirm reproducibility. Table 5 below shows the results (average values) of the rocking cell tests.

TABLE 5

Test results as anti-agglomerant in rocking-cell tests

| Test | Ammonium salt | Minimum Effective Dose Rate (vol.-%, based on water phase) |
|---|---|---|
| 17 | AS 1 | 0.35% |
| 18 | AS 2 | 0.35% |
| 19 | AS 3 | 0.50% |
| 20 | AS 4 | 0.60% |
| 21 | AS 5 | 0.55% |
| 22 | AS 6 | 0.55% |
| 23 | AS 7 | 0.50% |
| 24 | AS 8 | 0.6% |
| 25 | AS 9 | 0.50% |
| 26 | AS 10 + AS 3 (1:1) | 0.60% |
| 27 (comp.) | AS 13 | 0.70% |
| 28 (comp.) | AS 15 | 0.75% |
| 29 (comp.) | AS 16 | 0.90% |

Testing of Water Quality Upon Phase Separation of Gas and Fluid Phase

For assessment of the water quality obtained upon depressurization and separation of the gas form hydrocarbon and aqueous phase, samples (25 resp. 45 ml) of the crude oils characterized in table 6 where filled into graduated 120 ml glas bottles and filled to 100 ml with tap water. The bottles were placed in a heating bath of 100 F (37.8° C.) for 1 hour. Afterwards, the amount of anti-agglomerant given in tables 7 and 8 (based on total volume of the sample) was added and the bottles where combined in a box and shaken 200 times. Afterwards, the bottles were placed again in the heating bath. The water separation (measured in mL) and the water quality were rated after 5 min and 120 min of incubation time. Water quality was rated visually using the following grading:

Water Quality:
1=Clear and bright
2=Slight Haze
3=Hazy
4=Opaque

TABLE 6

Characterization of test oils

|  | Oil A | Oil B |
|---|---|---|
| API gravity | 30.9° | 21.8° |
| Saturates | 23.11% | 27.82% |
| Aromatics | 32.36% | 54.71% |
| Resins | 35.08% | 14.50% |
| Asphaltenes | 7.27% | 2.97% |

The oils were characterized by their contents of saturates, aromatics, resins and asphaltenes. The SARA analysis was made using a Iatroscan TLC-FID according to standard method IP 469.

As can be recognized from the test results, the method using N,N-dialkylammoniumalkyl fatty acid amide salts produced by amidation of a N,N-dialkylaminoalkylamine with a fatty acid according to the invention requires lower additive dosage rates than comparable methods according to the state of the art. Furthermore, the reduced viscosity of these amide salts eases application to the fluid to be treated. Additionally, the method allows for an improved water quality upon phase separation. These are distinct improvements over the prior art.

TABLE 7

Test results on water quality in Oil A

| | | | Water/oil (75/25 vol.-%) | | | | Water/oil (55/45 vol.-%) | | | |
|---|---|---|---|---|---|---|---|---|---|---|
| | | | water separation | | water quality | | water separation | | water quality | |
| Test | Ammonium salt | Dosage [vol.-%] | 5 min | 120 min | 5 min | 120 min | 5 min | 120 min | 5 min | 120 min |
| 30 | AS 1 | 0.5 | 52 ml | 72 ml | 1 | 1 | 42 ml | 53 ml | 1 | 1 |
| 31 | AS 1 | 1.0 | 55 ml | 70 ml | 1 | 1 | 40 ml | 49 ml | 1 | 1 |
| 32 | AS 2 | 0.5 | 53 ml | 72 ml | 1 | 1 | 43 ml | 52 ml | 1 | 1 |
| 33 | AS 2 | 1.0 | 60 ml | 73 ml | 1 | 1 | 40 ml | 50 ml | 1 | 1 |
| 34 | AS 5 | 0.5 | 49 ml | 70 ml | 1 | 1 | 41 ml | 52 ml | 1 | 1 |
| 35 | AS 5 | 1.0 | 58 ml | 71 ml | 1 | 1 | 42 ml | 49 ml | 1 | 1 |
| 36 (comp.) | AS 13 | 0.5 | 44 ml | 65 ml | 3 | 2 | 40 ml | 50 ml | 1-2 | 1 |
| 37 (comp.) | AS 13 | 1.0 | 47 ml | 68 ml | 3 | 2 | 35 ml | 45 ml | 2-3 | 1-2 |
| 38 (comp.) | AS 16 | 0.5 | 42 ml | 61 ml | 3 | 3 | 38 ml | 46 ml | 2 | 1-2 |
| 39 (comp.) | AS 16 | 1.0 | 45 ml | 64 ml | 4 | 3 | 33 ml | 43 ml | 3 | 2 |

TABLE 8

Test results on water quality in Oil B

| | | | Water/oil (75/25 vol.-%) | | | | Water/oil (55/45 vol.-%) | | | |
|---|---|---|---|---|---|---|---|---|---|---|
| | | | water separation | | water quality | | water separation | | water quality | |
| Test | Ammonium salt | Dosage [vol.-%] | 5 min | 120 min | 5 min | 120 min | 5 min | 120 min | 5 min | 120 min |
| 40 | AS 1 | 0.5 | 44 ml | 57 ml | 2 | 1 | 20 ml | 24 ml | 1 | 1 |
| 41 | AS 1 | 1.0 | 48 ml | 59 ml | 2 | 1 | 22 ml | 28 ml | 2 | 1 |

TABLE 8-continued

Test results on water quality in Oil B

| | | | Water/oil (75/25 vol.-%) | | | | Water/oil (55/45 vol.-%) | | | |
|---|---|---|---|---|---|---|---|---|---|---|
| | | | water separation | | water quality | | water separation | | water quality | |
| Test | Ammonium salt | Dosage [vol.-%] | 5 min | 120 min | 5 min | 120 min | 5 min | 120 min | 5 min | 120 min |
| 42 | AS 1 | 2.0 | 53 ml | 60 ml | 3 | 1 | 25 ml | 37 ml | 2 | 1 |
| 43 | AS 4 | 0.5 | 40 ml | 52 ml | 2 | 1 | 18 ml | 24 ml | 1 | 1 |
| 44 | AS 4 | 1.0 | 45 ml | 56 ml | 2 | 1 | 21 ml | 25 ml | 2 | 1 |
| 45 | AS 4 | 2.0 | 45 ml | 59 ml | 3 | 1 | 25 ml | 30 ml | 2 | 2 |
| 46 | AS 7 | 0.5 | 42 ml | 63 ml | 2 | 1 | 20 ml | 25 ml | 1 | 1 |
| 47 | AS 7 | 1.0 | 47 ml | 60 ml | 2 | 1 | 23 ml | 31 ml | 2 | 1 |
| 48 | AS 7 | 2.0 | 50 ml | 65 ml | 3 | 1 | 28 ml | 40 ml | 2 | 2 |
| 49 | AS 8 | 0.5 | 43 ml | 57 ml | 2 | 1 | 20 ml | 25 ml | 1 | 1 |
| 50 | AS 8 | 1.0 | 47 ml | 62 ml | 2 | 1 | 20 ml | 29 ml | 2 | 2 |
| 51 | AS 8 | 2.0 | 49 ml | 65 ml | 3 | 1 | 25 ml | 33 ml | 2 | 2 |
| 52 (comp.) | AS 13 | 0.5 | 40 ml | 50 ml | 4 | 2 | n.d. | 20 ml | 4 | 2 |
| 53 (comp.) | AS 13 | 1.0 | 45 ml | 52 ml | 3 | 2 | n.d. | 5 ml | 4 | 3 |
| 54 (comp.) | AS 13 | 2.0 | 42 ml | 49 ml | 4 | 3 | n.d. | 5 ml | 4 | 3 | n.d. = not detectable

The invention claimed is:

1. A method for inhibiting the agglomeration of gas hydrates, comprising the step of injecting at least one anti-agglomerant comprising at least one N,N-dialkyl-ammoniumalkyl fatty acid amide represented by the formula (I)

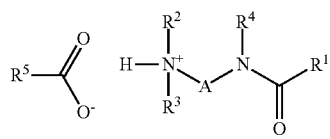

wherein
R$^1$ is an alkyl or alkenyl group having from 7 to 21 carbon atoms,
R$^2$ and R$^3$ are each independently an alkyl group containing 1 to 10 carbon atoms, or together form an optionally substituted ring having 5 to 10 ring atoms, wherein the ring may carry up to 3 substituents,
R$^4$ is hydrogen or an alkyl group having 1 to 6 carbon atoms,
R$^5$ is hydrogen, methyl, ethyl, ethenyl, or 2-propenyl and A is an alkylene group having two or three carbon atoms, into a fluid comprising gas, water and oil under conditions prone to the formation of gas hydrates,
wherein the at least one N,N-dialkyl-ammoniumalkyl fatty acid amide represented by the formula (I) is produced by the condensation reaction of at least one fatty acid with at least one N,N-dialkylamino alkyl amine and subsequent neutralization with at least one carboxylic acid, and
wherein the at least one carboxylic acid used for neutralization is selected from the group consisting of formic acid, acetic acid, propionic acid, acrylic acid, methacrylic acid and mixtures thereof, and
wherein the at least one anti-agglomerant is essentially free of glycerol.

2. The method according to claim 1, wherein the at least one fatty acid has the formula (III)

R$^1$—COOH (III)

wherein R$^1$ is an alkyl or alkenyl group having from 7 to 21 carbon atoms.

3. The method according to claim 2, wherein R$^1$ is an alkyl or alkenyl group having 12 or 14 carbon atoms.

4. The method according to claim 1, wherein at least 60 mol-% of the at least one fatty acid has 12 to 14 carbon atoms.

5. The method according to claim 1, wherein R$^1$ is linear.

6. The method according to claim 1, wherein the at least one N,N-dialkylamino alkyl amine has the general formula (IV)

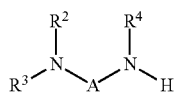

wherein
R$^2$ and R$^3$ are each independently an alkyl group containing 1 to 10 carbon atoms, or together form an optionally substituted ring having 5 to 10 ring atoms, wherein the ring may carry up to 3 substituents,
R$^4$ is hydrogen or an alkyl group having 1 to 6 carbon atoms, and
A is an alkylene group having two or three carbon atoms.

7. The method according to claim 1, wherein the at least one fatty acid and the at least one N,N-dialkylaminoalkylamine are reacted in a molar ratio of between 3:1 and 1:3.

8. The method according to claim 1, wherein the at least one anti-agglomerant is injected into the fluid prone to the formation of gas hydrates prior to formation of gas hydrates.

9. The method according to claim 1, wherein R$^2$ and R$^3$ are each alkyl having from 1 to 4 carbon atoms.

10. The method according to claim 1, wherein R$^4$ is H.

11. The method according to claim 9, wherein R$^4$ is H.

12. The method according to claim 1, wherein R$^1$ is alkyl or alkenyl having from 7 to 17 carbon atoms.

13. The method according to claim 1, wherein R$^1$ is alkyl or alkenyl having from 9 to 17 carbon atoms.

14. The method according to claim 11, wherein R$^1$ is alkyl or alkenyl having from 7 to 17 carbon atoms.

15. The method according to claim 11 wherein R$^1$ is alkyl or alkynyl having from 9 to 17 carbon atoms.

* * * * *